United States Patent [19]

Pelosi, Jr.

[11] 3,946,049

[45] Mar. 23, 1976

[54] 5-PHENYL-2-FURAMIDOXIMES
[75] Inventor: Stanford S. Pelosi, Jr., Norwich, N.Y.
[73] Assignee: Morton-Norwich Products, Inc., Norwich, N.Y.
[22] Filed: Apr. 3, 1975
[21] Appl. No.: 564,769

[52] U.S. Cl. ........ 260/347.2; 260/347.7; 260/347.8; 424/285; 260/346.1 R
[51] Int. Cl.² ........................................ C07D 307/66
[58] Field of Search .............................. 260/347.7

[56] References Cited
OTHER PUBLICATIONS
Lossen, Berichte, Vol. 17, pp. 1587–1589 (1884).
Migridichian, Organic Synthesis, Vol. 1, p. 410 (1957).

*Primary Examiner*—Harry I. Moatz
*Attorney, Agent, or Firm*—Anthony J. Franze

[57] ABSTRACT

A series of 5-phenyl-2-furamidoximes are useful as antidepressants.

20 Claims, No Drawings

5-PHENYL-2-FURAMIDOXIMES

This invention is concerned with a series of 5-phenyl-2-furamidoximes of the formula:

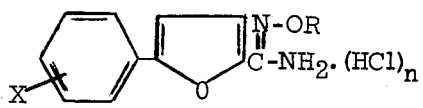

wherein X represents hydrogen, nitro, amino, 4-chloro, 4-methyl, 4-methylthio, 4-hydroxy, 4-benzyloxy, 4-acetyl, 4-(1-hydroxyethyl), 4-methoxy, and 4-dimethylamino; R represents hydrogen or methyl; and n represents 0, 1, or 2. These compounds are useful as antidepressants. Their useful antidepressant activity is exhibited in warm blooded animals under the standard ptosis-anti-tetrabenazine test. Thus, when administered perorally in suspension or aqueous solution in doses ranging from 25 to 50 mg/kg to mice shortly prior to intraperitoneal administration of from 1–10 mg/kg of tetrabenazine, ptosis induced by tetrabenazine is curtailed to the extent of from 50–100%.

the furamidoximes of this invention are prepared as illustrated in the following schema:

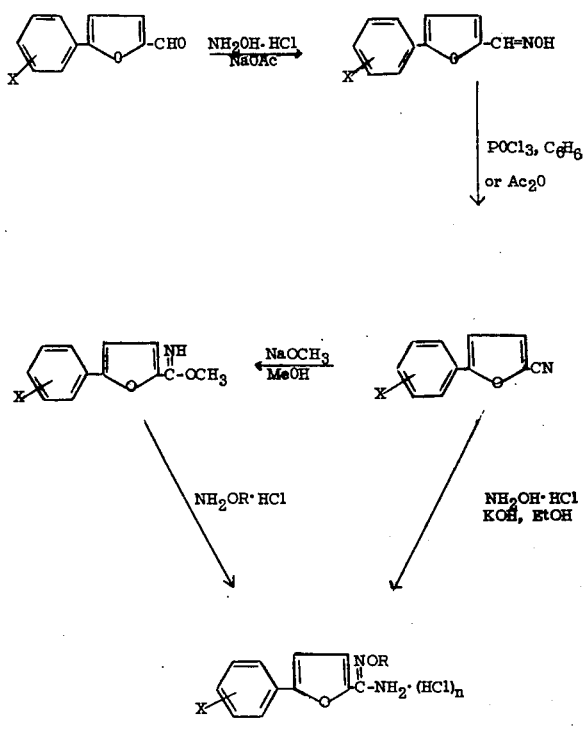

In the above schema, R and n have the significance previously ascribed.

The preparation of the amidoximes of this invention is more fully described in the following examples.

EXAMPLE I 5-(p-Chlorophenyl)-2-furamidoxime

A. 5-(p-Chlorophenyl)-2-furaldehyde Oxime

A mixture of 21 g (0.10 mole) of 5-(p-chlorophenyl)-2-furaldehyde, 14 g (0.20 mole) of hydroxylamine hydrochloride, 16.5 g (0.20 mole) of anhydrous sodium acetate, 350 ml of 95% ethanol, and 35 ml of water was heated under reflux for 3½ hours. After cooling, the mixture was poured into 1 l. of cold water. The solid which was deposited was collected by filtration and dried in 50° oven overnight to give 22 g (100%) of 5-(p-chlorophenyl)-2-furladehyde oxime. One recrystallization from an isopropanol-H$_2$O mixture gave an analytical sample, m.p. 139°–141°.

Anal. Calcd. for C$_{11}$H$_8$ClNO$_2$: C, 59.61; H, 3.64; N, 6.32. Found: C, 59.60; H, 3.57; N, 6.28.

B. 5-(p-Chlorophenyl)-2-furonitrile

A solution of 6.9 g (0.045 mole) of phosphorus oxychloride in 10 ml of benzene was added dropwise over 0.5 hours to a stirred, refluxing solution of 20 g (0.09 mole) of A in 350 ml of benzene. The reaction mixture was heated under reflux for 2 hours, cooled and filtered. The filtrate was washed with 5% of sodium bicarbonate solution, with water, and dried over MgSO$_4$. Solvent was removed on a rotary evaporator to give 16 g of residual solid. The solid was dissolved in hot MeOH, and water was added to turbidity. The black oily material which was deposited was separated by filtration and discarded. The filtrate was cooled to give a tan solid which was collected by filtration and dried in a 60° oven; weight was 12 g (65%), m.p. 76°–77°.

Anal. Calcd. for C$_{11}$H$_6$ClNO: C, 64.88; H, 2.97; N, 6.88. Found : C, 64.73; H, 2.99; N, 6.91.

C. 5-(p-Chlorophenyl)-2-furamidoxime

A mixture of 51 g (0.25 mole) of 5-(p-chlorophenyl)-2-furonitrile, 19 g (0.27 mole) of hydroxylamine hydrochloride, 18 g (0.27 mole) of potassium hydroxide and 750 ml of absolute ethanol was heated under reflux for 1 hour. The reaction mixture was concentrated on a rotary evaporator and cooled in ice overnight. The solid was collected by filtration and washed with anhydrous ether to give 43 g (73%). Two recrystallizations from absolute ethanol gave an analytical sample, m.p. 167°–169°.

Anal. Calcd. for C$_{11}$H$_9$ClN$_2$O$_2$: C, 55.82; H, 3.83; N, 11.84. Found : C, 55.44; H, 3.78; N, 11.72.

EXAMPLE II 5-(p-Nitrophenyl)-2-furamidoxime Hydrodhloride

A mixture of 97 g (0.45 mole) of 5-(p-nitrophenyl)-2-furonitrile, 34 g (0.49 mole) of hydroxylamine hydrochloride, 27 g (0.49 mole) of KOH and 1450 ml of absolute ethanol was refluxed for one hour, cooled and filtered. The solid was stirred in dilute HCl/H$_2$O, and was filtered and air dried to yield 86 g (67%). An analytical sample was prepared by drying a sample in the vacuum pistol at room temperature, m.p. 230°.

Anal. Calcd. for C$_{11}$H$_9$N$_3$O$_4$.HCl: C, 46.57; H, 3.55; N, 14.82. Found: C, 46.43; H, 3.59; N, 14.41.

EXAMPLE III 5-(p-Aminophenyl)-2-furamidoxime

A mixture of 55 g (0.19 mole) of the compound of Example II, 500 ml of CH$_3$OH and one teaspoon of 5% Pd/C (50% H$_2$O) was shaken on the Parr apparatus with the theoretical amount of H₂ being absorbed. The catalyst was removed by filtration and the solvent removed on the Calab evaporator leaving a residual solid which was washed in refluxing acetonitrile. The resulting solid was then washed in 1 N NaOH solution and air dried to yield 22 g (52%). An analytical sample was prepared by drying a sample at the temperature of refluxing $CHCl_3$ in the vacuum pistol, m.p. 180°–183°.

Anal. Calcd. for $C_{11}H_{11}N_3O_2$: C, 60.82; H, 5.10; N, 19.35. Found: C, 60.67; H, 5.23; N, 19.00.

EXAMPLE IV

5-(p-Methylphenyl)-2-furamidoxime

A mixture of p-toluidine (216 g, 2.0 moles) in $H_2O$ (400 ml) and concentrated HCl (540 ml) was diazotized by dropwise addition of solution of $NaNO_2$ (144 g, 2.08 moles) in $H_2O$ (400 ml) with the pot temperature kept below 10°. The mixture was stirred for ½ hour and furfural (246 g, 2.56 moles) was added followed by a solution of $CuCl_2$ (46 g) in $H_2O$ (300 ml). The stirred mixture was heated at 40°–50° for 5 hours and stored overnight at room temperature. The product was extracted with ether (1200 ml), dried overnight over $MgSO_4$ and Darco, filtered and the filtrate stripped of solvent under reduced pressure. The residue was distilled in vacuo, collecting the product at 160°–/1.4 mm Hg; yield: 70 g (19%) of 5-(p-methylphenyl)-2-furaldehyde.

A solution of hydroxylamine hydrochloride (26 g, 0.38 mole) in $H_2O$ (65 ml) was added to a solution of 5-(p-methylphenyl)-2-furaldehyde (70 g, 0.38 mole) in absolute alcohol (200 ml), then stirred for 20 minutes and cooled overnight. The oxime was collected by filtration; yield: 60 g (79%).

A stirred mixture of 5-(p-methylphenyl)-2-furaldehyde oxime (60 g, 0.39 mole) and benzene (1200 ml) was heated to reflux and a solution of $POCl_3$ (11 ml) in benzene (30 ml) was added dropwise over 15 minutes. The mixture was refluxed for an additional 1½ hours and filtered while hot. The filtrate was washed with 5% $NaHCO_3$ (700 ml), $H_2O$ (700 ml), dried over $MgSO_4$ and Darco, filtered and the filtrate stripped of solvent under reduced pressure; yield: 42 g (76%) of nitrile.

A mixture of 9.0 g (0.050 mole) of 5-(p-methylphenyl)-2-furonitrile, 3.75 g (0.054 mole) of hydroxylamine hydrochloride, 3.5 g (0.054 mole) of potassium hydroxide and 125 ml of absolute ethanol was refluxed for 2 hours and then cooled in an ice bath. The insoluble material was filtered and discarded. The filtrate was added to a mixture of ice/$H_2O$ and the resulting solid was filtered and stirred in 150 ml of refluxing hexane. The mixture was filtered hot and the solid was air dried to yield 7 g (65%). An analytical sample was prepared by recrystallizing a sample form hexane/Darco and drying in the vacuum pistol at the temperature of refluxing $CHCl_3$, m.p. 139°–141°.

Anal. Calcd. for $C_{12}H_{12}N_2O_2$: C, 66.65; H, 5.59; N, 12.96. Found: C, 66.49; H, 5.62; N, 12.80.

EXAMPLE V

5-(p-Benzyloxyphenyl)-2-furamidoxime

A. 5-(p-Benzyloxyphenyl)-2-furaldehyde

A mixture of 236 g (1.0 mole) of p-benzyloxyaniline hydrochloride in 1.5 l of water and 230 ml of conc. HCl was warmed on a steam bath for 1½ hours. No solution was effected. The mixture was then cooled down to 0°–5° and a solution of 76 g (1.1 mole) of sodium nitrite in 500 ml of water was added in about 1 hour while keeping the temperature at 4°–7°. The mixture was allowed to stir further for an additional 45 minutes while the temperature gradually rose to 10°. Furfural (192 g, 2 moles) and 55 g of cupric chloride dihydrate in a minimum amount of water was added and the mixture was allowed to stir at ambient temperature overnight. Solid started to separate after 2 days of stirring. The solid was collected, washed well with water. The filtrate and the water washings were combined and allowed to stir for an additional 4 days while more solid separated. The dark gummy solids were combined, triturated with ether, filtered and air dried. Repeated recrystallizations from hot cyclohexane gave 48.5 g (17.5%).

B. 5-(p-Benzyloxyphenyl)-2-furonitrile

A mixture of 34.6 (0.125 mole) of 5-(p-benzyloxyphenyl)-2-furaldehyde, 17.3 g (0.25 mole) of hydroxylamine hydrochloride and 20.4 g (0.25 mole) of anhydrous sodium acetate in 900 ml of ethanol and 80 ml of water was heated at reflux for 5 hours. After cooling, the mixture was poured into ice water and solid separated very readily. The solid was collected, washed with water and air dried. the yield of oxime was 33 g (91%).

A mixture of 38.5 g (0.131 mole) of the above oxime in 400 ml of acetic anhydride was heated at reflux for 3 hours. After cooling, the reaction solution was poured onto crushed ice with stirring. Oily material gradually solidified. The solid was collected, washed with water and dried to give 40.5 g of crude product. Recrystallization from 4 l of hexane gave 30 g (83%) of 5-(p-benzyloxyphenyl)-2-furonitrile.

C. 5-(p-Benzyloxyphenyl-2-furamidoxime

A mixture of 30 g (0.11 mole) of 5-(p-benzyloxyphenyl)-2-furonitrile, 8.3 g (0.12 mole) of hydroxylamine hydrochloride, 8 g (0.12 mole) of KOH and 330 ml of absolute ethanol was refluxed for 1½ hours, cooled in an ice bath and filtered. The solid obtained was recrystallized from 95% ethanol to yield 19 g (56%). An analytical sample was obtained by drying a sample in the vacuum pistol at the temperature of refluxing $CHCl_3$, m.p. 145°–146°.

Anal. Calcd. for $C_{18}H_{16}N_2O_3$: C, 70.12; H, 5.23; N, 9.09. Found : C, 69.85; H, 5.24; N, 9.00.

EXAMPLE VI

5-(p-Hydroxyphenyl)-2-furamidoxime

A mixture of 15 g (0.048 mole) of the compound of Example V, 1 tsp. of 5% Pd/C, 50% $H_2O$, and 135 ml of methanol was shaken under hydrogen pressure with the theoretical amount of $H_2$ being absorbed. The catalyst was removed by filtration and the solvent removed on the Calab evaporator to give a residual solid. The solid was refluxed in 750 ml of ethyl acetate, cooled in an ice bath and the insoluble material removed by filtration. The filtrate was reduced to 300 ml volume on the Calab evaporator and then diluted with hexane. The resulting solid was filtered and air dried to yield 5.4 g (46%). An analytical sample was prepared by dissolving a sample in refluxing ethyl acetate and adding hexane to the cloud point. This procedure was repeated three times, m.p. 157°–158°.

Anal. Calcd. for $C_{11}H_{10}N_2O_3$: C, 60.54; H, 4.62; N, 12.84. Found : C, 60.30; H, 4.69; N, 12.54.

EXAMPLE VII

5-Phenyl-2-furamidoxime

A solution of hydroxylamine hydrochloride (20 g, 0.29 mole) in $H_2O$ (50 ml) was added to a solution of 5-phenyl-2-furaldehyde (50 g, 0.29 mole) in ethanol (150 ml) with stirring. The light yellow product was collected by filtration, yield: 48 g (89%) of oxime. A sample was recrystallized from isopropanol, m.p. 182°–184°.

Anal. Calcd. for $C_{11}H_9NO_2$: C, 70.58; H, 4.64; N, 7.48. Found : C, 70.35; H, 4.83; N, 7.37.

A stirred mixture of 5-phenyl-2-furaldehyde oxime (39 g, 0.21 mole) and benzene (850 ml) was heated under reflux, and a solution of $POCl_3$ (7 ml, 0.1 mole) in benzene (20 ml) was added dropwise over 30 minutes. The mixture was refluxed for an additional 1½ hours and filtered while hot. The filtrate was washed with 5% $NaHCO_3$ (800 ml), $H_2O$ (800 ml), dried over $MgSO_4$ and Darco, and filtered. The filtrate was stripped of solvent under reduced pressure; yield: 29 g (88%) of nitrile.

A mixture of 10 g (0.059 mole) of 5-phenyl-2-furonitrile, 4.1 g (0.060 mole) of hydroxylamine hydrochloride, 4.0 g (0.060 mole) of potassium hydroxide, and 150 ml of absolute ethanol was refluxed for 2½ hours, cooled to room temperature, and then added to 750 ml of ice/$H_2O$. the resulting solid was washed in water and dried at 60° to yield 10 g (84%), m.p. 118°–120°.

Anal. Calcd. $C_{11}H_{10}N_2O_2$: C, 65.33; H, 4.98; N, 13.86. Found: C, 65.42; H, 4.97; N, 13.53.

EXAMPLE VIII

5-(p-Methylthiophenyl)-2-furamidoxime

A solution of 4-methylthioaniline hydrochloride (175 g, 1.0 mole) in $H_2O$ (200 ml) and concentrated HCl (450 ml) was diazotized by dropwise addition of a solution of $NaNO_2$ (70 g) in $H_2O$ (200 ml) with the pot temperature kept below 10°. The mixture was stirred for ½ hour, then furfural (192 g, 2.0 moles) was added followed by a solution of $CuCl_2$ (23 g) in $H_2O$ (100 ml). The mixture was stirred in ambient temperature for 2 days. The product was extracted with ether (1800 ml) in portions, dried over $MgSO_4$ and Darco, filtered; the filtrate stripped of solvent under reduced pressure. The residue was distilled in vacuo, collecting the 5-(p-methylthiophenyl-2-furaldehyde at 180°–220° (1–3 mm Hg), yield: 52 g (24%).

A solution of hydroxylamine hydrochloride (16.5 g, 0.24 mole) in $H_2O$ (35 ml) was added to a solution of 5-(p-methylthiophenyl)-2-furaldehyde (52 g, 0.24 mole) in absolute alcohol (300 ml) and stirred for 1 hour. The oxime was collected by filtration, yield: 41 g (73%).

A stirred mixture of 5-(p-methylthiophenyl)-2-furaldehyde oxime (41 g, 0.18 mole) and benzene (300 ml) was heated to reflux and a solution of $POCl_3$ (8 ml) in benzene (40 ml) was added dropwise over 20 minutes. The mixture was refluxed for an additional 1½ hours and filtered while hot. The filtrate was washed with 5% $HaHCO_3$ (500 ml), $H_2O$ (500 ml), dried over $MgSO_4$ and Darco, filtered; the filtrate was stripped of solvent under reduced pressure, yield: 31 g (80%) of nitrile.

A mixture of 13 g (0.060 mole) of 5-(p-methylthiophenyl)-2-furonitrile, 4.5 g (0.065 mole) of hydroxylamine hydrochloride, 4.2 g (0.065 mole) of KOH, and 160 ml of absolute ethanol was refluxed for 1½ hours and then kept overnight at room temperature. The insoluble material was removed by filtration and discarded. The filtrate was added to ice/water and the resulting solid was dissolved in refluxing ethyl acetate, Darcoed, and filtered. The filtrate was heated to reflux and hexane was added to the cloud point. This mixture was cooled in an ice bath with the resulting solid being filtered and air dried to yield 10 g (67%). An analytical sample was prepared by drying a sample in the vacuum pistol at the temperature of refluxing $CHCl_3$, m.p. 148°–150°.

Anal. Calcd. for $C_{12}H_{12}N_2O_2S$: C, 58.04; H, 4.87; N, 11.28. Found: C, 57.90; H, 4.70; N, 11.00.

EXAMPLE IX

O-Methyl-5-(4-nitrophenyl)-2-furamidoxime

A mixture of 2.14 g (0.010 mole) of 5-(4-nitrophenyl)-2-furonitrile, 0.59 g (0.011 mole) of $NaOCH_3$ and 40 ml of anhydrous $CH_3OH$ was heated to near reflux with dissolution. After heating for 1 hour, the reaction was cooled to room temperature and 0.92 g (0.011 mole) of methoxyamine hydrochloride was added. The resulting mixture was refluxed for 2½ hours and then cooled in an ice bath. The solid was filtered, washed with water and dried in the vacuum pistol at the temperature of refluxing $CHCl_3$ to yield 1.9 g (73%), m.p. 151°–153°.

Anal. Calcd. for $C_{12}H_{11}N_3O_4$: C, 55.17; H, 4.24; N, 16.09. Found : C, 54.87; H, 4.15; N, 15.77.

EXAMPLE X

5-[4-(1-Hydroxyethyl)phenyl]-2-furamidoxime

A. 5-(p-Acetylphenyl)-2-furonitrile 5-(p-Acetylphenyl)-2-furaldehyde (43 g, 0.2 mole) was dissolved in a mixture of 2.8 l of ethanol and 150 ml of dimethylformamide by warming on a steam bath with stirring. The slightly cloudy brown solution was cooled down to 35° and then 13.9 g (0.2 mole) of hydroxylamine hydrochloride in a minimum amount of water (50 ml) was added in about 5 minutes. The cloudy solution was allowed to stir at ambient temperature for 5¾ hours. After overnight standing, the reaction mixture was poured onto crushed ice. Light brown solid separated and was collected, washed with water and air dried. More solid separated from the filtrate and was also collected. The combined yield of the oxime was 43 g (93.5%). The solid was placed in 500 ml of acetic anhydride and heated at reflux for 4 hours. After cooling, the reaction mixture was poured onto crushed ice and allowed to hydrolyze gradually. The brown solid was collected, washed well with water and air dried to give 37.5 g of crude material. Recrystallization from 1.1 l of methylcyclohexane gave 22 g (52.5%) of 5-(p-acetylphenyl)-2-furonitrile.

Recrystallization of 1 g from 100 ml of methylcyclohexane gave 0.4 g of analytically pure material, m.p. 122°–125°.

B. 5-[4-(1-Hydroxyethyl)phenyl]-2-furonitrile

A solution of 46 g (0.22 mole) of 5-(4-acetylphenyl)-2-furonitrile in 800 ml of 95% dioxane/$H_2O$ was treated portionwise with 8.3 g (0.22 mole) of $NaBH_4$ while keeping the temperature below 20° by means of an ice bath. The resulting solution was stirred at ambient temperature for 2½ hours and then added to an ice/$H_2O$ mixture. After standing 48 hours, the reaction mixture was extracted with ether and the combined ethereal extracts dried over MgSO$_4$. The ether was removed on the Calab evaporator yielding 27 g (58%) of product as a residual oil.

C. 5-[4-(1-Hydroxyethyl)phenyl]-2-furamidoxime

A mixture of 27 g (0.13 mole) of 5-[4-(1-hydroxyethyl)phenyl]-2-furonitrile, 8.3 g (0.13 mole) of NH$_2$OH.HCl, 8.5 g (0.13 mole) of KOH and 200 ml of absolute ethanol was refluxed for 2 hours, cooled to room temperature, and added to ice/H$_2$O with a semisolid forming. This material was extracted with ether and the combined ethereal extracts dried over MgSO$_4$. The ether was dissolved in ethyl acetate, and hexane was added to turbidity. The resulting mixture was warmed in a steam bath, cooled, filtered and air dried to yield 17 g (55%).

An analytical sample was prepared by treating a sample three times as above with ethyl acetate-hexane and drying in the vacuum pistol at room temperature, m.p. 159°–160°.

Anal. Calcd. for C$_{13}$H$_{14}$N$_2$O$_3$: C, 63.40; H, 5.73; N, 11.38. Found: C, 63.12; H, 5.73; N, 11.24.

EXAMPLE XI

O-Methyl-5-phenyl-2-furamidoxime

A mixture of 1.69 g (0.010 mole) of 5-phenyl-2furonitrile, 0.54 g (0.01 mole) of NaOCH$_3$, and 30 ml of anhydrous CH$_3$OH was refluxed for 1 hour. The resulting solution was cooled to room temperature and 0.84 g (0.010 mole) of methoxyamine hydrochloride was added. The resulting mixture was refluxed for 2 hours, and then cooled to room temperature. A small amount of solid was filtered and discarded. The filtrate was added to ice/H$_2$O and the resulting solid was filtered, and dried in the vacuum pistol at room temperature to yield 1.8 g (83%). An analytical sample was prepared by recrystallizing a sample from hexane/Darco and drying in the vacuum pistol at room temperature, m.p. 103°–104°.

Anal. Calcd. for C$_{12}$H$_{12}$N$_2$O$_2$: C, 66.65; H, 5.59; N, 12.96. Found : C, 66.64; H, 5.46; N, 13.00.

EXAMPLE XII 5-(4-Acetylphenyl)-2-furamidoxime

A mixture of 17.0 g (0.080) mole of 5-(4-acetylphenyl)-2-furonitrile, 4.24 g (0.080 mole) of NaOCH$_3$ and 300 ml of anhydrous CH$_3$OH was refluxed for 1 hour and then cooled to room temperature. After adding 5.16 g (0.080 mole) of NH$_2$OH.HCl, the reaction was stirred at room temperature for 2 hours at near reflux for 15 minutes and then cooled in an ice bath. The resulting solid was filtered, air dried, and recrystallized from ethyl acetate/Darco to yield 4.5 g (23%). An analytical sample was prepared by drying a sample in the vacuum pistol at the temperature of refluxing CHCl$_3$, m.p. 197°–199°.

Anal. Calcd. for C$_{13}$H$_{12}$N$_2$O$_3$: C, 63.93; H, 4.95; N, 11.47. Found: C, 63.77; H, 5.02 N, 11.15.

EXAMPLE XIII

O-Methyl-5-(4-aminophenyl)-2-furamidoxime

A mixture of 12.4 g (0.0475 mole) of the compound of Example IX, ½ tsp. of 5% Pd/C (50% H$_2$O), and 150 ml of CH$_3$OH was shaken under hydrogen pressure with the theoretical amount of H$_2$ being absorbed. The catalyst was removed by filtration and the filtrate was taken to dryness on the Calab evaporator yielding a residual solid. This solid was dissolved in refluxing ethyl acetate (Darco), filtered, and the filtrate treated with hexane. The resulting solid was filtered and air-dried to yield 6.0 g (55%). An analytical sample was prepared by drying a sample in the vacuum pistol at room temperature, m.p. 115°–117°.

Anal. Calcd. for C$_{12}$H$_{13}$N$_3$O$_2$: C, 62.32; H, 5.67; N, 18.10. Found: C, 61.93; H, 5.68; N, 18.01.

EXAMPLE XIV

O-Methyl-5-(2-nitrophenyl)-2-furamidoxime Hydrochloride

A mixture of 53.0 g (0.25 mole) of 5-(2-nitrophenyl)-2-furonitrile, 14.6 g (0.27 mole) of sodium methylate and 750 ml of anhydrous methanol was heated to reflux with dissolution. The solution was refluxed one hour, cooled to room temperature and 23.0 g (0.27 mole) of methoxyamine hydrochloride was added. This solution was refluxed for 2½ hours and the solvent was then removed on the Calab evaporator yielding a residual oil. This oil was dissolved in ethyl acetate, washed with water, and dried over MgSO$_4$. The solvent then removed on the Calab evaporator and the residual oil was dissolved in ether. The ethereal solution was treated with ethereal/HCl. The resulting sticky solid was filtered, recrystallized from nitromethane, and air dried to yield 21 g (29%). An analytical sample was prepared by recrystallizing a sample from acetonitrile and drying in the vacuum pistol at room temperature, m.p. 182°–184°.

Anal. Calcd. for C$_{12}$H$_{11}$N$_3$O$_4$: C, 48.41; H, 4.06; N, 14.12. Found: C, 48.14; H, 3.84; N, 14.09.

EXAMPLE XV 5-(2-Nitrophenyl)-2-furamidoxime Hydrochloride

A mixture of 5-(2-nitrophenyl)-2-furonitrile (34 g, 0.16 mole), KOH (9.5 g, 0.17 mole), hydroxylamine hydrochloride (11.5 g, 0.165 mole) and absolute alcohol (400 ml) was heated under reflux for 2 hours. The reaction mixture was cooled in ice, and the insoluble material was collected by filtration. The solvent was removed on a rotary evaporator, and the residual oil (44 g) was triturated with water several times. It was dissolved in anhydrous ether (ca. 2l. ) and the insoluble material was removed by filtration. Gaseous HCl was introduced into the filtrate yielding a solid that was collected by filtration and washed with anhydrous ether to give 33 g (73%). An analytical sample, m.p. 205°–206°, was obtained by recrystallization from isopropanol.

Anal. Calcd. for C$_{11}$H$_9$N$_3$O$_4$.HCl: C, 46.57; H, 3.55; N, 14.82. Found: C, 46.99; H, 3.62; N, 14.82.

EXAMPLE XVI 5-(4-Methoxyphenyl)-2-furamidoxime Hydrochloride

A. 5-(4-Methoxyphenyl)-2-furaldehyde

A 5l. three-necked flask equipped with stirrer, thermometer and dropping funnel was charged with water (150ml), concentrated HCl (400 ml) was introduced, followed by p-anisidine (185 g, 1.5 moles). A solution of sodium nitrite (108 g, 1.56 moles) in water (300 ml) was introduced dropwise maintaining −10° to −5°C. Furfural (184 g, 1.92 moles) was introduced followed by a solution of CuCl$_2$.2H$_2$O (46 g) in water (300 ml). The reaction mixture was heated to 53° with hot water maintaining 53°–68° for 2.5 hours. After cooling to room temperature overnight, the reaction mixture was extracted with ether (1800 ml). The dried (MgSO$_4$) extract was evaporated in a rotary evaporator, and the residue was distilled under reduced pressure to give 70 g of black semi-solid product (b.p. 160°–190° at 2-5 mm).

B. 5-(p-Methoxyphenyl)-2-furaldehyde Oxime

A 250 ml Erlenmeyer flask was charged with 5-(4-methoxyphenyl)-2-furaldehyde (40 g, 0.20 mole) and absolute alcohol (125 ml). A solution of hydroxylamine hydrochloride (14 g, 0.20 mole) in water (25 ml) was added to this suspension. This mixture was stirred for 1 hour, cooled, filtered and washed with isopropanol, yielding 28 g (65.2%).

C. 5-(p-Methoxyphenyl)-2-furonitrile

A 500 ml three-necked flask equipped with stirrer, thermometer and reflux condenser was charged with 5-(p-methoxyphenyl)-2-furaldehyde oxime (28 g, 0.129 mole) and acetic anhydride (317 ml). This mixture was refluxed (138°) for 3 hours. After cooling to room temperature overnight, the green solution was poured into ice water (ca. 2l. ) with stirring. When the ice melted, the solid was collected by filtration, washed with water, and dried to give 26 g.

D. 5-(4-Methoxyphenyl-2-furamidoxime Hydrochloride

A 500 ml three-necked flask equipped with a stirrer and reflux condenser was charged with 5-(p-methoxyphenyl)-2furonitrile (13 g, 0.065 mole), KOH (4.2 g, 0.075 mole) and absolute alcohol (200 ml). This mixture was refluxed for 2.5 hours and allowed to cool to ambient temperature. After cooling, small amount of insoluble material was removed by filtration. The solvent was removed in a rotary evaporator and the residue was suspended in anhydrous ether (ca. 900 ml). Gaseous HCl was introduced and the mixture was stirred for 1 hour. The solid was collected by filtration and washed with anhydrous ether to give 13.5 g (77.2%) of product. An analytical sample was obtained by recrystallization from S.D.A. No. 32 containing some HCl, m.p. 205°–206°.

Anal. Calcd. for $C_{12}H_{12}N_2O_3 \cdot HCl$: C, 53.64; H, 4.88; N, 10.43. Found: C, 53.44; H, 4.95; N, 10.19.

EXAMPLE XVII 5-(2-Aminophenyl)-2-furamidoxime Dihydrochloride

A mixture of the compound of Example XV (14.2 g 0.05 mole), 5% Pd/C (50% H$_2$O) (1 teaspoon), and anhydrous methanol (300 ml) was shaken in a Parr apparatus until the theoretical amount of hydrogen was absorbed. The catalyst was removed by filtration and washed with anydrous methanol. Gaseous HCl was introduced into the filtrate with cooling in ice. The solid was collected by filtration and washed with anhydrous ether to give 10.8 g (75%) of product. An analytical sample, m.p. 238°–239°, was obtained by drying in an Abderhalden.

Anal Calcd. for $C_{11}H_{11}N_3O_2 \cdot 2HCl$: C, 45.53; H, 4.52; N, 14.48. Found: C, 45.77; H, 4.75; N, 14.41.

EXAMPLE XVIII

O-Methyl-5-(2-aminophenyl-2-furamidoxime Dihydrochloride Monohydrate

A mixture of 11.4 g (0.038 mole) of the compound of Example XIV, ½ tsp. of Pd/C (50% H$_2$O), and 150 ml of methanol was shaken under hydrogen pressure with the theoretical amount of hydrogen being absorbed. The catalyst was removed by filtration, and the filtrate taken to dryness on the Calab evaporator yielding a residual oil. This oil was dissolved in methanol, treated with methanolic/HCl and diluted with ether with a solid forming. This solid was again treated as above and then air dried to yield 7.0 g (57%). An analytical sample was prepared by dissolving a sample of the above solid in methanol (Darco), filtering, treating the filtrate with ethereal HCl, and drying the resulting solid in the vacuum pistol at room temperature, m.p. 216°–218°.

Anal. Calcd. for $C_{12}H_{13}N_3O_2 \cdot 2HCl \cdot H_2O$: C, 44.75; H, 5.32; N, 13.05. Found: C, 45.01; H, 5.32; N, 13.40.

EXAMPLE XIX 5-(4-Dimethylaminophenyl)-2-furamidoxime Dihydrochloride

A. 5-(4-Dimethylaminophenyl)-2-furaldehyde Oxime

A 12 l. four-necked flask equipped with stirrer, thermometer, and dropping funnel was charged with conc'd. HCl (4120 ml) N,N-Dimethyl-p-phenylenediamine (1013 g, 7.45 moles) was introduced slowly yielding a dark red solution. A solution of sodium nitrite (505 g, 7.3 moles) in water (2060 ml) was introduced dropwise maintaining −10° to −5°C. 2-Furaldehyde (705 g, 7.35 moles) was introduced at once followed by a solution of $CuCl_2 \cdot 2H_2O$ (286 g) in water (1040 ml). The reaction mixture was stirred for 4.5 days and 1 gallon of ether was added. The water layer was separated and treated with "Darco" at ambient temperature. After filtering, a solution of hydroxylamine hydrochloride (518 g, 7.45 moles) in water (1370 ml) was introduced. The reaction mixture was heated to 58°C and stirring was continued for 3 days at ambient temperature. The black semi-solid was filtered and suspended in water and made basic with a saturated Na$_2$CO$_3$ solution. After stirring for 1.5 hours the black solid obtained by filtration was stirred with ether (ca. 4l. ). The dried (MgSO$_4$) solution was evaporated in a rotary evaporator. The residual dark solid was partially dissolved in benzene and precipitated with hexane to give 11 g of oxime.

B. 5-(4-Dimethylaminophenyl)-2-furonitrile

A 500 ml three-necked flask equipped with stirrer, reflux condenser and dropping funnel was charged with 5-(4-dimethylaminophenyl)-2-furaldehyde oxime (10.5 g, 0.046 mole) and benzene (250 ml). A solution of POCl$_3$ (3.75 ml, 0.04 mole) in benzene (100 ml) was introduced dropwise and the reaction mixture was refluxed for 3 hours. The content of the flask was poured into an Erlenmeyer, ice cooled, and treated with water (120 ml), ether (400 ml) and solid NaHCO$_3$ until it was basic. The water layer was discarded. The dried (MgSO$_4$) organic layer was evaporated in rotary evaporator, and the residue was triturated with a minimum of anhydrous ether (ca. 25 ml) yielding 3.8 g of nitrile.

C. 5-(4-Dimethylaminophenyl)-2-furamidoxime Dihydrochloride

A 250 ml three-necked flask equipped with stirrer and reflux condenser was charged with 5-(4-dimethylaminophenyl)-2-furonitrile (4.0 g, 0.019 mole), hydroxylamine hydrochloride (1.5 g, 0.022 mole), KOH (1.25 g, 0.0223 mole) and absolute alcohol (100 ml). The reaction mixture was refluxed for 2.5 hours. It was cooled and filtered. The solvent was removed leaving a gummy solid that was suspended in anhydrous ether (ca. 200 ml). Gaseous HCl was introduced to saturation, yielding 3.8 g (63.2%). An analytical sample (m.p. 220°–222°) was obtained by recrystallization from a MeOH-ether mixture.

Anal. Calcd. for $C_{13}H_{15}N_3O_2 \cdot 2HCl$: C, 49.07; H, 5.38; N, 13.21. Found: C, 48.90; H, 5.45; N, 13.15.

What is claimed is:

1. A compound of the formula:

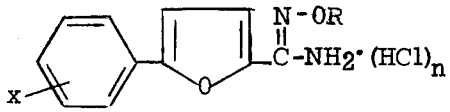

wherein X represents hydrogen, nitro, amino, 4-chloro, 4-methyl, 4-methylthio, 4-hydroxy, 4-benzyloxy, 4-acetyl, 4-(1-hydroxyethyl), 4-methoxy, and 4-dimethylamino; R represents hydrogen or methyl; and n represents 0, 1, or 2.

2. The compound 5-(p-chlorophenyl)-2-furamidoxime.

3. The compound 5-(p-nitrophenyl)-2-furamidoxime hydrochloride.

4. The compound 5-(p-aminophenyl)-2furamidoxime.

5. The compound 5-(p-methoxyphenyl)-2-furamidoxime.

6. The compound 5-(p-benzyloxyphenyl)-2-furamidoxime.

7. The compound 5-(p-hydroxyphenyl)-2-furamidoxime.

8. The compound 5-phenyl-2furamidoxime.

9. The compound 5-(p-methylthiophenyl)-2-furamidoxime.

10. The compound O-methyl-5-(4-nitrophenyl)-2-furamidoxime.

11. The compound 5-[4-(1-hydroxyethyl)phenyl]-2-furamidoxime.

12. The compound O-methyl-5-phenyl-2-furamidoxime.

13. The compound 5-(4-acetylphenyl)-2-furamidoxime.

14. The compound O-methyl-5-(4-aminophenyl)-2-furamidoxime.

15. The compound O-methyl-5-(2-nitrophenyl)-2-furamidoxime hydrochloride.

16. The compound 5-(2-nitrophenyl)-2-furamidoxime hydrochloride.

17. The compound 5-(4-methoxyphenyl)-2furamidoxime hydrochloride.

18. The compound 5-(2-aminophenyl)-2furamidoxime dihydrochloride.

19. The compound O-methyl-5-(2-aminophenyl)-2-furamidoxime dihydrochloride monohydrate.

20. The compound 5-(4-dimethylaminophenyl)-2-furamidoxime dihydrochloride.

* * * * *